(12) United States Patent
Berardi et al.

(10) Patent No.: US 8,150,624 B2
(45) Date of Patent: Apr. 3, 2012

(54) SYSTEM AND METHOD FOR TRACKING A MOVING PERSON

(75) Inventors: Stephen A. Berardi, Woodland Hills, CA (US); Joseph A. Fax, Los Angeles, CA (US)

(73) Assignee: Northrop Grumman Systems Corporation, Los Angeles, CA (US)

( * ) Notice: Subject to any disclaimer, the term of this patent is extended or adjusted under 35 U.S.C. 154(b) by 733 days.

(21) Appl. No.: 12/268,687

(22) Filed: Nov. 11, 2008

(65) Prior Publication Data

US 2010/0121572 A1    May 13, 2010

(51) Int. Cl.
G01C 21/10 (2006.01)
G01C 21/16 (2006.01)
G01C 21/00 (2006.01)

(52) U.S. Cl. ........ 701/500; 701/472; 701/479; 701/480; 701/499; 701/509; 701/510

(58) Field of Classification Search .................. 701/210, 701/216, 217, 220, 411, 472, 479, 480, 494, 701/499, 500, 509, 510
See application file for complete search history.

(56) References Cited

U.S. PATENT DOCUMENTS

| | | | |
|---|---|---|---|
| 5,583,776 A | 12/1996 | Levi et al. | |
| 6,522,266 B1 | 2/2003 | Soehren et al. | |
| 6,789,425 B2* | 9/2004 | Akieda et al. | 73/514.31 |
| 6,813,582 B2* | 11/2004 | Levi et al. | 702/141 |
| 6,826,477 B2* | 11/2004 | Ladetto et al. | 701/217 |
| 7,387,611 B2* | 6/2008 | Inoue et al. | 600/595 |
| 7,398,151 B1 | 7/2008 | Burrell et al. | |
| 7,428,472 B2 | 9/2008 | Darley et al. | |
| 7,505,865 B2* | 3/2009 | Ohkubo et al. | 702/142 |
| 7,805,274 B2* | 9/2010 | Wang et al. | 702/130 |
| 7,827,000 B2* | 11/2010 | Stirling et al. | 702/141 |
| 2001/0015123 A1* | 8/2001 | Nishitani et al. | 84/615 |
| 2003/0018430 A1 | 1/2003 | Ladetto et al. | |
| 2004/0064286 A1 | 4/2004 | Levi et al. | |
| 2005/0096569 A1 | 5/2005 | Sato et al. | |
| 2007/0260418 A1 | 11/2007 | Ladetto et al. | |
| 2008/0154495 A1 | 6/2008 | Breed | |

(Continued)

FOREIGN PATENT DOCUMENTS

EP        1 199 544 A1    5/2002

(Continued)

OTHER PUBLICATIONS

Matsubara, C., "Development of a Portable Long-Term Heart Rate Body Temperature and Step Rate Recorder" (Abstract only), Journal of Kyoto Prefectural University of Medicine, vol. 100, No. 6, p. 623-630, 1991.*

(Continued)

*Primary Examiner* — Nicholas D Rosen
(74) *Attorney, Agent, or Firm* — Tarolli, Sundheim, Covell & Tummino LLP

(57) ABSTRACT

Systems and methods are provided for tracking a moving person. The system comprises a controller configured to receive acceleration data that characterizes an acceleration of the moving person in three dimensions. The controller comprises a step rate component that determines a step rate for the person based on a vertical component of the acceleration data. The controller also comprises a body offset component that determines a body offset angle based on a spectral analysis of the acceleration data and the step rate. The controller further comprises a velocity component that determines a reference velocity vector based on the body offset angle and the step rate.

20 Claims, 6 Drawing Sheets

U.S. PATENT DOCUMENTS

2008/0262728 A1 10/2008 Lokshin et al.
2009/0005975 A1* 1/2009 Forstall et al. ............... 701/209

FOREIGN PATENT DOCUMENTS

| | | |
|---|---|---|
| EP | 1 764 582 A3 | 3/2007 |
| EP | 1 770 370 A3 | 4/2007 |
| EP | 1 988 492 A1 | 11/2008 |
| WO | WO 2009/007498 A1 | 1/2009 |

OTHER PUBLICATIONS

Heyn, A., et al., "The Kinematics of the Swing Phase Obtained from Accelerometer and Gyroscope Measurements" (Abstract only), Proceedings of the 18$^{th}$ Annual International Conference of the IEEE Engineering in Medicine and Biology Society, Bridinging Disciplines for Biomedicine, vol. 2, p. 463-464, IEEE, New York, 1997.*

Han, J.H., et al., "Gait Analysis for Freezing Detection in Patients with Movement Disorder Using Three Dimensional Acceleration System" (Abstract only), Annual International Conference of the IEEE Engineering in Medicine and Biology Society—Proceedings, IEEE, 2003.*

UK Search Report for corresponding GB 0913084.0, completed Aug. 21, 2009.

* cited by examiner

SYSTEM AND METHOD FOR TRACKING A MOVING PERSON

TECHNICAL FIELD

The present invention relates generally to tracking systems, and more particularly to systems and methods for tracking a moving person.

BACKGROUND OF THE INVENTION

An inertial measurement unit (IMU), is the main component of inertial guidance systems that can be employed in a variety of different tracking applications, including tracking of personnel (e.g., infantry units). An IMU works by sensing motion, including the type, rate, and direction of that motion using a combination of accelerometers and gyroscopes. The data collected from these detectors allows a computer to track a person or unit's position, using a method known as dead reckoning. These types of guidance systems typically suffer from accumulated error, because the guidance system is continually adding detected changes to its previously-calculated positions (e.g., dead reckoning). Any errors in measurement, however small, are accumulated from point to point. This leads to 'drift', or an ever-increasing difference between where system sensed that it is located, and the actual location of the system.

SUMMARY OF THE INVENTION

One aspect of the present invention is related to a system for tracking a moving person. The system comprises a controller configured to receive acceleration data that characterizes an acceleration of the moving person in three dimensions. The controller comprises a step rate component that determines a step rate for the person based on a vertical component of the acceleration data. The controller also comprises a body offset component that determines a body offset angle based on a spectral analysis of the acceleration data and the step rate. The controller further comprises a velocity component that determines a reference velocity vector based on the body offset angle and the step rate.

Another aspect of the present invention is related to a system for tracking a moving person. The system comprises means for providing three dimensional acceleration data that characterizes acceleration of the moving person in three dimensional space. Means for determining a step rate of the moving person based on a vertical component of the three dimensional spectral data is also included. Means for analyzing the spectral data and the step rate to determine a magnitude of a body offset angle is further included.

Still another aspect of the invention is related to a method for tracking a moving person. The methodology comprises determining a step rate for the moving person. The methodology also comprises determining a body offset angle for the moving person based on a detected heading of the moving person and a spectral analysis of three dimensional acceleration data that characterizes an acceleration of the moving person in three dimensional space.

DETAILED DESCRIPTION OF THE DRAWINGS

An inertial measurement unit (IMU) can be employed to determine a position of a user (e.g., a person) when other systems, such a global positioning system (GPS) are unavailable. A person can employ an inertial measurement unit (IMU) to receive Data from motion detectors (e.g., accelerometers, gyroscopes, etc.) that can be provided to a controller. The motion data can have, for example, a vertical component (e.g., a 'Z' component), a first horizontal component (e.g., an 'X' component) and a second horizontal component (e.g., a 'Y') component. The Z component of the motion data can be employed to determine a step rate of the user. Additionally, the controller can employ spectral analysis of the X and Y components of the motion data to determine a body offset of the user. The step rate and the body offset can be employed to determine a reference velocity vector for the user.

The reference velocity vector can be provided to a Kalman Filter. Additionally, a navigation velocity calculated by an integration of the motion data can be provided to the Kalman Filter. The Kalman Filter can recursively compare the reference velocity vector and the navigation velocity vector to determine a stride length error for the user. The stride length error and the reference velocity vector can be provided to a dead reckoning component that can determine the position of the user based on the last previous known or calculated position of the user.

Figure 1:
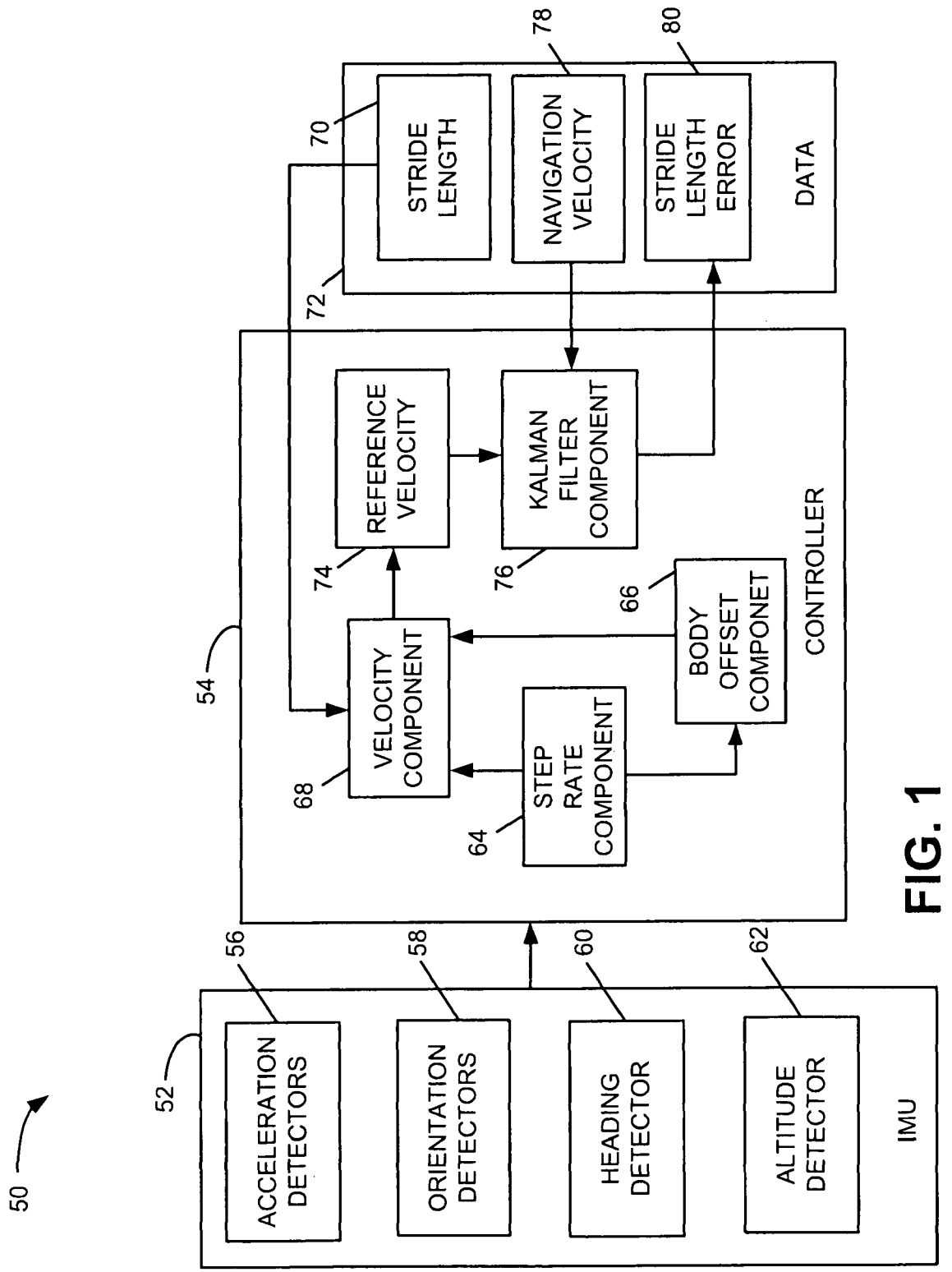
FIG. 1 illustrates an exemplary navigation system for tracking a person in accordance with an aspect of the invention.

FIG. 1 illustrates an exemplary navigation system 50 for tracking a person in accordance with an aspect of the present invention. The navigation system 50 can be implemented as hardware (e.g., an application specific integrated circuit chip), software (e.g., computer executable instructions) executing on hardware (e.g., a processor and memory) or a combination thereof. The navigation system 50 can include an IMU 52 that can provide motion data that characterizes detected motions of the user to a controller 54. The IMU 52 can include, for example, acceleration detectors 56 (e.g., accelerometers) that can detect an acceleration of the user in three dimensions. The IMU 52 can also include orientation detectors 58 (e.g., gyroscopes) that can detect a change in the user's orientation (e.g., pitch, yaw and roll). Additionally, a heading detector 60 (e.g., a magnetometer) can be included that can detect a heading of the user, and an altitude detector 62 (e.g., an altimeter) can be included to detect an altitude of the user.

The IMU 52 motion data provided to the controller 54 can include, for example, a vertical component (e.g., a 'Z' component) that characterizes acceleration detected in a vertical direction. The IMU 52 motion data can also include a first horizontal component (e.g., an 'X' component) that characterizes acceleration detected in a first horizontal direction and a second horizontal component (e.g., a 'Y' component) that characterizes acceleration detected in a second horizontal direction offset by about 90 degrees from the first horizontal direction.

A step rate component 64 of the controller 54 can employ the 'Z' component of the motion data to determine a step rate of the user. Typically, when the user takes a step, the user will have acceleration in the vertical (e.g., 'Z') direction. Thus, a detection of the rate of this vertical acceleration can characterize a step rate of user.

The step rate of the user can be provided to a body offset component 66 of the controller 54. The body offset component 66 can employ a spectral analysis of the X and Y component of the motion data to determine a magnitude of a body offset angle of the user. Additionally, the body offset component 66 can employ heading data provided by the IMU 52 to determine a sign of the body offset angle. The heading data can characterize, for example, a heading (e.g., direction) that the user is facing. The body offset component 66 can employ the magnitude and sign of the body offset angle to determine a velocity unit vector that characterizes a direction of travel of the user.

The velocity unit vector can be provided to a velocity component 68. The step rate and a stride length 70 can also be provided to the velocity component 68. The stride length 70 can for example, be set by the user, and can be stored in data storage (e.g., random access memory (RAM)) 72. The velocity component 68 can be configured to multiply the stride length 70 and the step rate to determine a speed of the user. The speed of the user can be multiplied with the velocity vector unit to provide a reference velocity vector 74 that characterizes the velocity (e.g., the speed and direction) of the user. The reference velocity vector 74 can be provided to a Kalman Filter component 76.

The Kalman Filter component 76 can be configured as a Kalman Filter that is implemented as an efficient recursive filter that estimates the state of a dynamic system from a series of incomplete and noisy measurements. In the present example, the Kalman Filter component 76 receives the reference velocity vector 74 and a navigation velocity vector 78 from the data storage 72. The navigation velocity vector 78 can represent, for example an integration of at least a portion of the motion data over a predetermined period of time (e.g., 120 seconds). In some implementations, a sign of the velocity vector 78 can be employed as the sign of the body offset angle. The Kalman Filter component 76 can recursively filter the reference velocity vector 74 and the navigation velocity vector 78 to provide a stride length error 80 that characterizes the difference between the navigation velocity vector and the reference velocity vector 74. The stride length error 80 can be stored, for example, in the data storage 72.

The stride length error 80 and the reference velocity vector 74 can be employed, for example, by a dead reckoning component (not shown) to update a determined position of the user based on the last previous known or calculated position of the user. The navigation system 50 can be employed, for example, concurrently and/or intermittently with a GPS system, such that the position of the user can be determined when GPS signals are unavailable (e.g., indoors, extreme weather, etc.).

Figure 2:
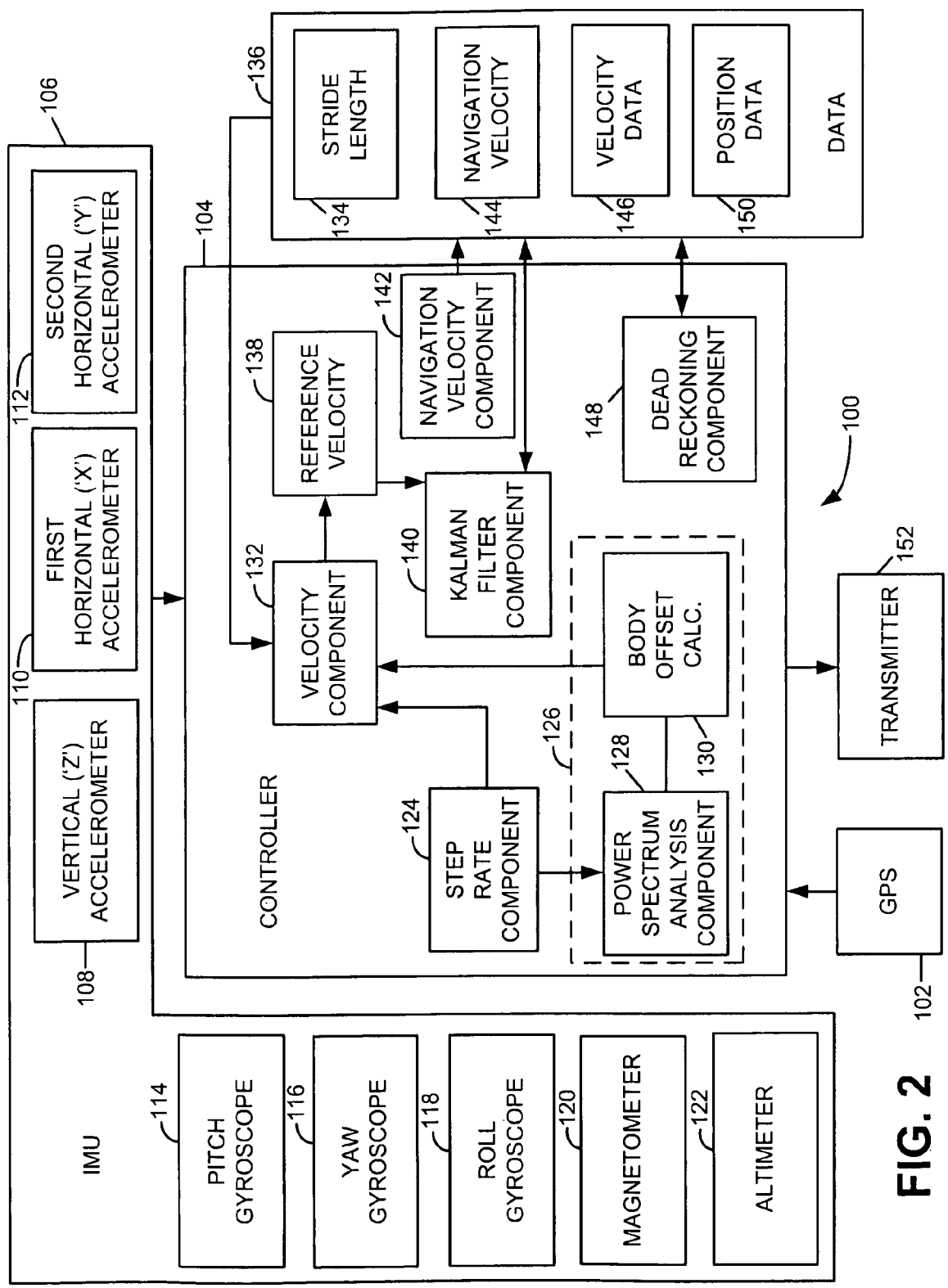
FIG. 2 illustrates another exemplary navigation system for tracking a person in accordance with an aspect of the invention.

FIG. 2 illustrates another exemplary navigation system 100 in accordance with an aspect of the invention. The navigation system 100 could be employed, for example, for tracking personnel (e.g., infantry). The navigation system 100 can include a GPS 102 that receives positional signals from satellites to determine a position of a user, and provides the position information to a controller 104. There are times, however, that the satellite signals may not be received by the GPS, such as when a user of the navigation system 100 is indoors or severe weather interferes with the signal. Accordingly, the navigation system 100 can include features that allow the navigation system 100 to calculate the position of the user when the GPS system 102 fails to provide accurate position information.

To calculate the position of the user, the navigation system 100 can include, for example, an IMU 106 that provides motion data and heading data to the controller 104. While FIG. 2 depicts the IMU 106 and the controller 104 as being separate entities, one skilled in the art will appreciate that the IMU 106 and the controller 104 could be an integrated unit (e.g., an integrated circuit chip, a printed circuit board with one or more integrated circuit chips, etc.). The motion data could include, for example, a vertical (e.g., a 'Z') component, a first horizontal (e.g., an 'X') component, and a second horizontal (e.g., a 'Y') component. The 'Z' component can, for example, characterize acceleration of the IMU 106 in the vertical direction. In such a situation, the 'X' component could characterize acceleration of the IMU 106 in a horizontal direction, while the 'Y' component can characterize acceleration of the IMU 106 a horizontal direction offset by about 90 degrees from the 'X' component. The heading data could characterize a heading of a user (e.g., a person) carrying/wearing the IMU 106 and/or the navigation system 100.

To provide the motion data, the IMU 106 can include, for example, a vertical (e.g., 'Z') accelerometer 108 that can detect acceleration of the user in the 'Z' direction. The IMU 106 can also include a first and second horizontal (e.g., 'X' and 'Y') accelerometers 110 and 112 that can detect acceleration in horizontal directions offset 90 degrees from each other. Additionally or alternatively, the IMU 106 can include a pitch gyroscope 114, a yaw gyroscope 116 and a roll gyroscope 118 that can detect changes of to the pitch, yaw and roll, respectively, of the IMU 106. The IMU 106 can employ the accelerometers 108, 110 and 112 and/or the gyroscopes 114, 116 and 118 to calculate the 'X', 'Y' and 'Z' components of the motion data.

The IMU 106 can also include a magnetometer 120 that can detect the heading of the user. The IMU 106 can employ the detected heading to provide the heading data to the controller 104. Additionally, in some embodiments, the IMU 106 can include an altimeter 122 that can detect an altitude of the user. In such embodiments, the IMU 106 can employ the detected altitude to increase accuracy of the detected heading.

In response to receiving the motion data and the heading data, a step rate component 124 of the controller 104 can determine a step rate for the user. Thus, the 'Z' component of the motion data can be employed to determine the step rate of the user. Accordingly, the step rate can be determined, for example, based on a frequency of the 'Z' component of the motion data.

The step rate can be provided to a body offset component 126 of the controller 104. The body offset component 126 can include a power spectrum analysis component 128 that can analyze a power spectrum of the X and Y components of the motion data to determine offset data. An example of the power spectrum for X and Y components of the motion data is illustrated as FIGS. 3 and 4.

Figure 3:
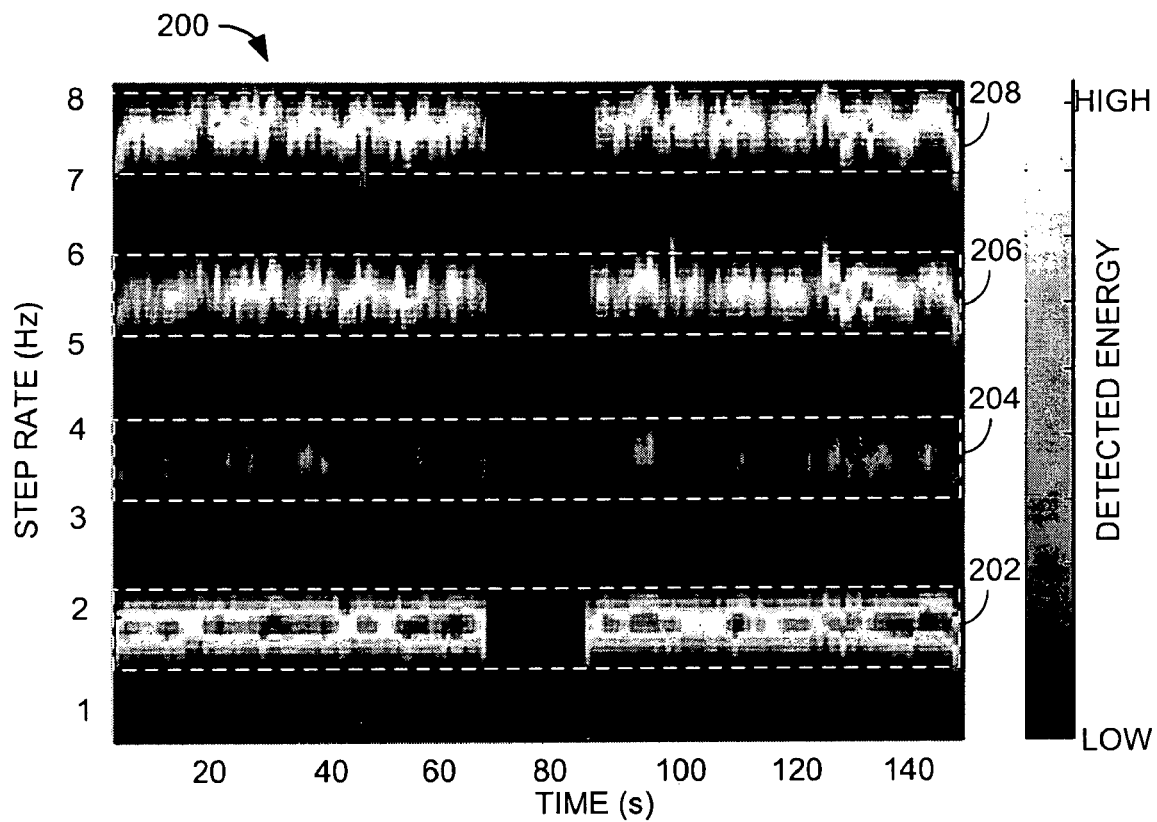
FIG. 3 represents a step rate plotted as a function of time in accordance with an aspect of the invention.

In FIG. 3, a graph 200 depicting a power spectrum of a first horizontal (e.g., 'X') component of motion data is illustrated. The graph 200 plots a signal strength detected at different step rates, in Hertz (HZ) as a function of time in seconds (s). In FIG. 2, four step signals at 202, 204, 206 and 208 are depicted. The step rate can be employed to determine an 'X' step signal of interest. In the present example, the step rate can be assumed to be about 2 steps per second, thus making the first step signal 202 the 'X' step signal of interest. The remaining step signals at 204, 206 and 208 can be harmonic signals that are not of interest.

In the present example, the step signal 202 of interest can be detected at about 2 Hz from about 1 second to about 65 seconds and again at about 85 seconds to about 160 seconds. When a person walks, that person typically accelerates and decelerates in a first direction (e.g., the direction that the person is walking). Thus, the step signal of interest 202 can indicate that a person is walking at a rate of about 2 steps per second from about 0 to about 65 seconds and again from about 85 seconds to about 160 seconds, while standing relatively still from about 65 seconds to about 85 seconds.

Figure 4:
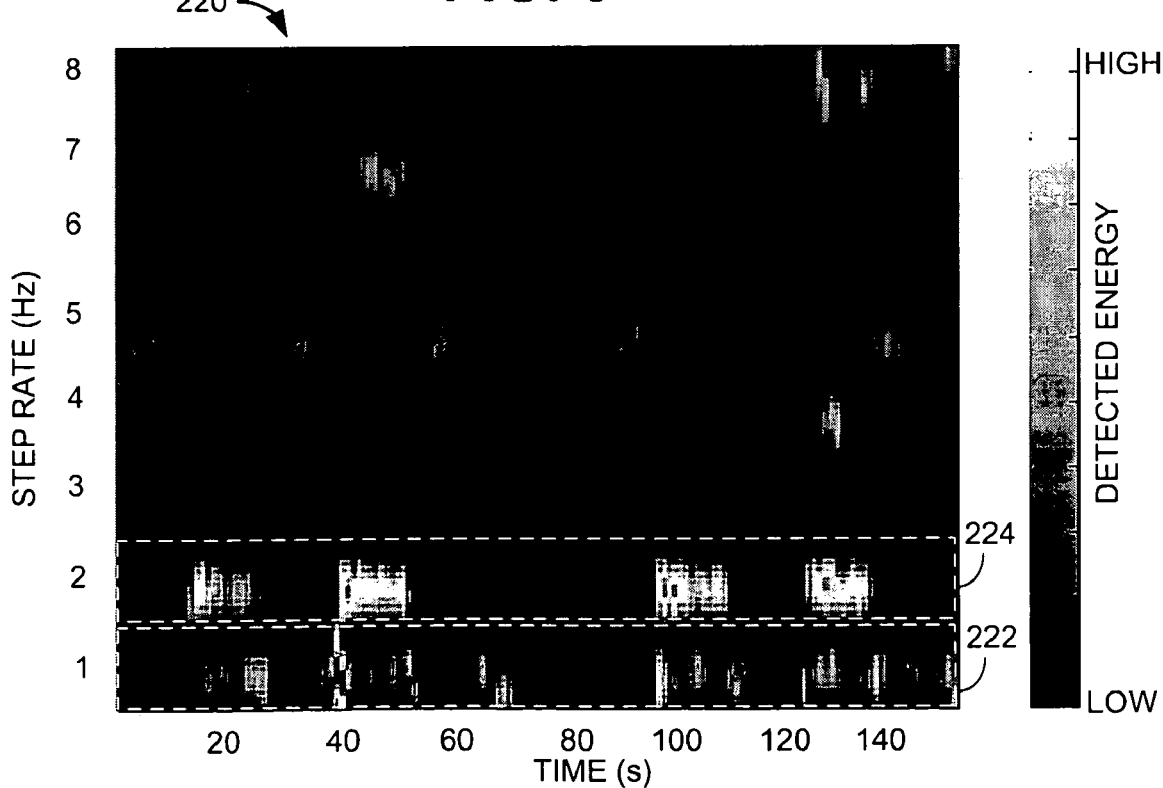
FIG. 4 represents another example of a step rate plotted as a function of time in accordance with an aspect of the invention.

FIG. 4 illustrates a graph 220 of a power spectrum for a second horizontal (e.g., 'Y') component of motion data that characterizes step signals offset about 90 degrees from the step signals illustrated in FIG. 3. The graph 220 plots a signal strength detected at different step rates, in Hertz (HZ) as a function of time in seconds (s). When a person walks, the person typically accelerates in a direction offset about 90 degrees from the first horizontal direction (e.g., side-to-side acceleration) at a rate of about ½ the step rate. Thus, the step rate can be employed to determine a 'Y' step signal of interest. As discussed above with respect to FIG. 3, in the present example, the step rate can be assumed to be about 2 steps per second, making a signal indicated at 222 with a step rate of about 0.5 steps per second the step rate of interest 222.

Additionally, the graph 220 depicts an intermittent step signal at 224. As is known, a person's torso can face a different direction than the person walks such as, when the person is talking to an adjacent person and walking simultaneously. The intermittent step signal 224 can indicate, for example, periods of time that the person's torso is twisted while walking in a different direction. Such periods of time can be identified by determining periods of time in the intermittent step signal 222 that have a significant signal strength at a step rate similar to the step rate of the step signal of interest 202 illustrated in FIG. 4 at intersecting times. The intersecting times can be referred to as "bleed over" since a portion of the step signal of interest 224 "bleeds over" to the intermittent signal 224 when the person's torso is facing a different direction than the person is walking.

In the present example, the graphs 200 and 220 of FIGS. 3 and 4 illustrate a situation where a person's torso is offset by about 20 degrees from the direction that the person is walking at a time from about 15 seconds to about 30 seconds and again from about 125 seconds to about 140 seconds. Additionally, in the present example, the person's torso is offset by about −20 degrees from about 40 seconds to about 55 seconds and again from about 100 seconds to about 115 seconds. This torso offset can be referred to as a body offset angle. The signal strength (shown via pixel intensity) of the intermittent signal 224 can increase proportionately to the body offset angle, while the strength signal of interest 202 (also shown via pixel intensity) can concurrently decrease proportionately (e.g., varies in inverse proportion) to the body offset angle.

As is shown in FIG. 4, spectral characteristics are substantially similar for body offset angles that have opposite signs, but equal magnitude. Referring back to FIG. 2, the power spectrum analysis component 128 can thus employ spectrum analysis to determine a magnitude of a body offset angle and provide that information to a body offset calculator 130. The body offset calculator 130 can employ the magnitude of body offset angle and directional data (provided by the IMU 106) to determine the body offset angle that defines a magnitude and sign of an angle corresponding to the direction of travel of the user. The body offset angle can be provided to a velocity component 132.

The velocity component 132 can also be configured to receive the step rate and a stride length 134 from a data storage 136. The data storage 136 could be implemented, for example, as RAM. The velocity component 132 can convert the magnitude and sign of the body offset angle into a velocity unit vector. The stride length 134 can be determined, for example, by the user. Additionally or alternatively, it is to be understood that the stride length 134 can be calibrated by a calibration system (not shown) of the navigation system 100. The velocity component 132 can be configured to multiply the stride length 134, the step rate and the velocity unit vector to determine a reference velocity 138 (e.g., a velocity vector) that characterizes the speed and direction of the user. The reference velocity 138 can be provided to a Kalman Filter component 140.

A navigation velocity component 142 can be employed to determine a navigation velocity 144. The navigation velocity component 142 can, for example, be employed to integrate the motion data provided from the IMU 106 over a predetermined time interval (e.g., 120 seconds), as is known in the art. The navigation velocity 144 can be stored in the data storage 136.

The Kalman Filter component 140 can access the navigation velocity 144 in the data storage 136. The Kalman Filter component 140 can employ a Kalman Filter analysis (e.g., recursive filtering) to recursively compare the reference velocity 138 to the navigation velocity 144 to determine a Kalman Filter Scale Factor error estimate, which can be referred to as stride length error. The Kalman Filter component 140 can store the reference velocity 138 and the stride length error as velocity data 146 in the data storage 136. In some implementations, a sign of the reference velocity 138 can be employed as the sign of the body offset angle.

A dead reckoning component 148 can be configured to detect a loss of position information provided by the GPS system 102. The dead reckoning component 148 can access the velocity data to obtain data for dead reckoning calculations. In response to such a loss of position information, the dead reckoning component 148 can be configured to calculate a reckoning velocity vector by employing the following equations:

$$[Vreck] = \begin{bmatrix} \cos(\psi) & \sin(\psi) \\ -\sin(\psi) & \cos(\psi) \end{bmatrix} \begin{bmatrix} Vcalc \\ 0 \\ 0 \end{bmatrix} \quad \text{Eq. 1}$$

$$Vcalc = \frac{(1.0 - KSF) * \text{Stride}}{T} \quad \text{Eq. 2}$$

where:
Vreck is the reckoning velocity
ψ is the sign and magnitude of the body offset angle;
Vcalc is the calculated velocity accounting for the stride length error;
KSF is the stride length error (the Kalman Filter Scale Factor error estimate);
Stride is the stride length;
T is the time interval for taking a step (e.g., inverse of the step rate);

Thus, by employing equations 1 and 2, the dead reckoning component 148 can calculate the reckoning velocity (Vreck). Additionally, the dead reckoning component 148 can also employ the position information from the last known or calculated position indicated by the GPS or the dead reckoning component 148 to determine an offset corrected position (e.g., an estimated or calculated position) of the user. Data characterizing the offset corrected position can be stored as position data 150 of the data storage 136. The controller 104 can provide the position data 150 to a transmitter 152 that can transmit the position data 150 to another entity (not shown) such as a hub.

The navigation system 100 can determine a position of the user whether or not the navigation system 100 receives position information from the GPS. Moreover, when position information is not provided by the GPS, the navigation system 100 can account for torso twisting of the user thereby allowing the user to walk in a normal manner without concern for loss of accuracy of the navigation system 100.

Figure 5:
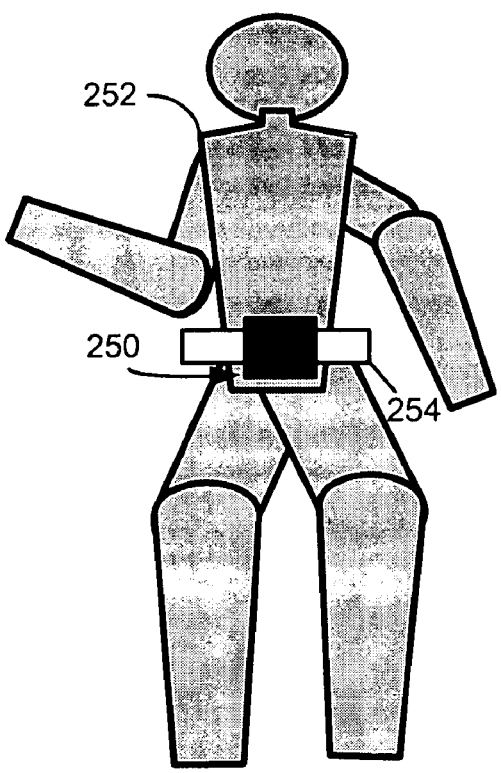
FIG. 5 illustrates an exemplary scenario of a person using a navigation system in accordance with an aspect of the invention.
Figure 6:
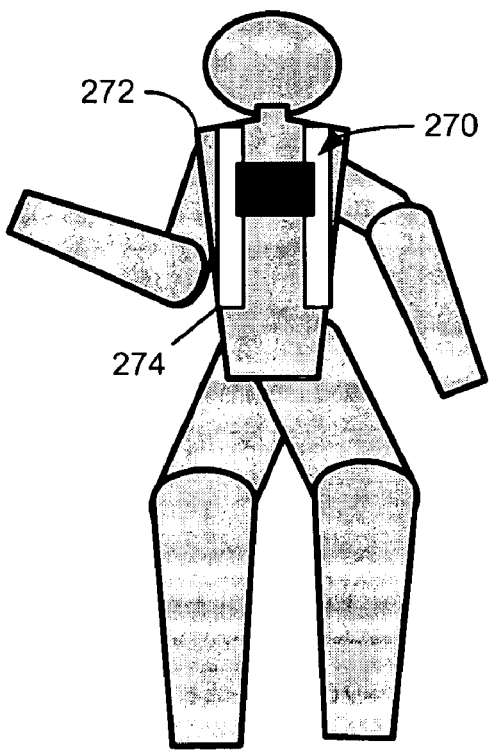
FIG. 6 illustrates another exemplary scenario of a person using a navigation system in accordance with an aspect of the invention.

FIGS. 5 and 6 illustrate examples of navigation systems 250 and 270 (e.g., the navigation system 100 illustrated in FIG. 2) affixed to a user 252 and 272 (e.g., a person) in accordance with aspects of the invention. The navigation system can be affixed to the person at or above the waist of the person. In FIG. 5, the navigation system 250 is affixed the waist of the person 252, such as on a belt 254. In FIG. 6, the navigation system 270 is affixed to the back of the person 272, such as on a backpack 274. Placement of the navigation system 250 and 270 at or above the waist of the person, such as shown in FIGS. 5 and 6, decreases the likelihood that the environmental conditions in which the navigation systems 250 and 270 operate (e.g., areas at or near water) will cause damage that might otherwise occur from placing the navigation systems 250 and 270 below the waist of the person, such as on the feet of the person.

Figure 7:
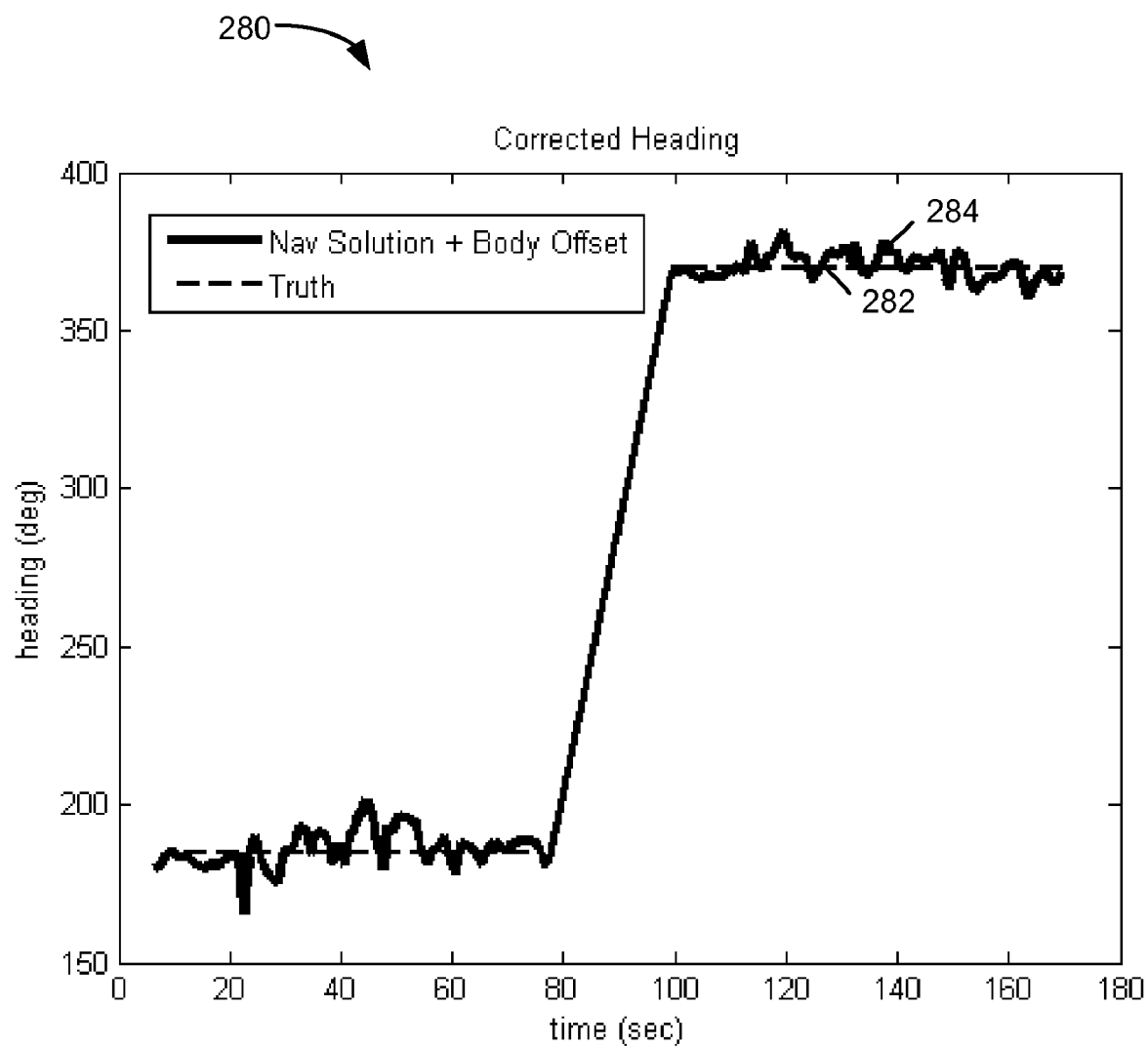
FIG. 7 represents a graph depicting test results of a navigation system in accordance with an aspect of the invention.

FIG. 7 illustrates an example of a graph 280 of test results of body offset detection for a navigation system (e.g., the navigation system 100 illustrated in FIG. 2) in accordance with an aspect of the invention. The graph 280 plots a detected heading in degrees as function of time in seconds for a test course. The course included a straight-line out and back walk (south then north) with a period of body offset of about 40 degrees in the middle of each leg of the course. The graph 280 includes a plot of an actual heading 282, as well as a plot of a calculated body offset angle 284 calculated by employment of spectral analysis and heading data. As is shown on the graph, the body offset angle calculated by the navigation system provides a relatively accurate estimate of the actual heading.

Figure 8:
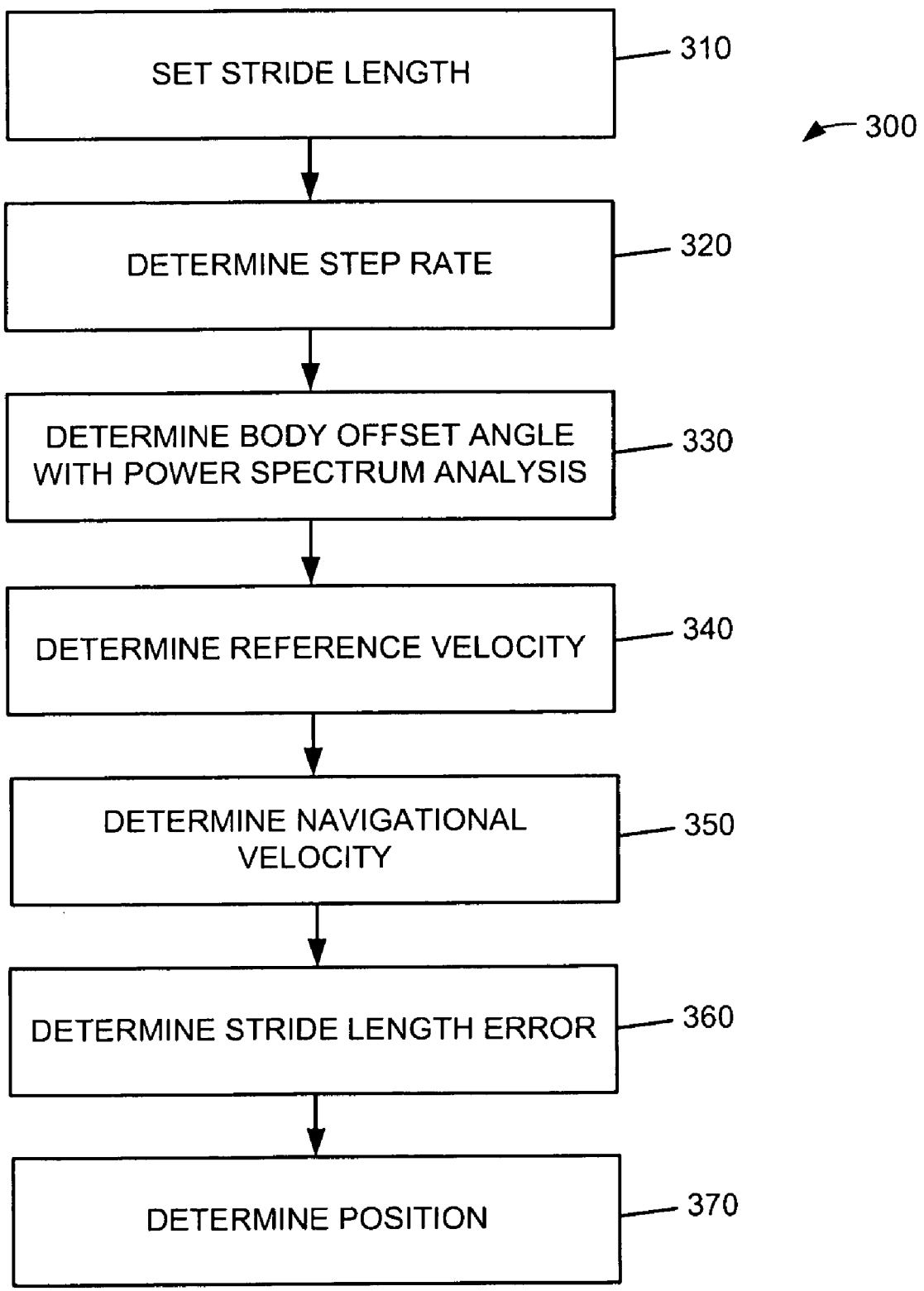
FIG. 8 illustrates an exemplary flowchart of a methodology in accordance with an aspect of the invention.

In view of the foregoing structural and functional features described above, methodologies will be better appreciated with reference to FIG. 8. It is to be understood and appreciated that the illustrated actions, in other embodiments, may occur in different orders and/or concurrently with other actions. Moreover, not all illustrated features may be required to implement a method.

FIG. 8 illustrates a flow chart of a methodology 300 for determining a position of a user (e.g., a person) employing a navigation system (e.g., the navigation system 100 illustrated in FIG. 2) in accordance with an aspect of the invention. At 310, a stride length that corresponds to a walking stride length of the user is set. The stride length can be set, for example, by the user, or can be determined (e.g., calibrated) automatically. At 320, the user's step rate can determined based on data characterizing the user's vertical acceleration (e.g., a 'Z' component).

At 330, the user's body offset angle can be determined. A magnitude of the body offset angle can be calculated based on a spectral analysis of the user's horizontal acceleration in a first direction, and a direction about 90 degrees offset from the first direction, which can be referred to as X and Y components of the user's acceleration. A sign of the body offset angle can be determined based on heading data that characterizes a heading of the user.

At 340, a reference velocity of the user based on the determined step rate and the determined body offset angle can be determined. The reference velocity can characterize the speed and direction of the user. At 350, a navigation velocity can be determined. The navigation velocity can be, for example, an integration of the X, Y and Z components of the user's acceleration over a predetermined amount of time (e.g., 120 seconds). In some implementations, a sign of the navigational velocity can be employed as the sign of the body offset angle. At 360, a stride length error can be determined. The stride length error can be based, for example, on a Kalman Filter analysis employed to recursively compare the reference velocity with the navigation velocity.

At 370, a position of the user can be determined. To calculate the position of the user, the Equations 1 and 2 can be employed to determine a reckoning velocity of the user. The reckoning velocity can be employed to calculate a position of the user based on the last known or calculated position of the user.

What has been described above includes exemplary implementations of the present invention. It is, of course, not possible to describe every conceivable combination of modules or methodologies for purposes of describing the present invention, but one of ordinary skill in the art will recognize that many further combinations and permutations of the present invention are possible. Accordingly, the present invention is intended to embrace all such alterations, modifications and variations that fall within the scope of the appended claims.

Having described the invention, the following is claimed:

1. A system for tracking a moving person, the system comprising:
   a controller configured to:
      receive acceleration data that characterizes an acceleration of the moving person in three dimensions and heading data that characterizes a heading of the moving person, wherein the controller comprises:
         a step rate component that determines a step rate for the person based on a vertical component of the acceleration data;
         a body offset component that determines a body offset angle and a velocity unit vector based on the heading data, the step rate and a spectral analysis of horizontal components of the acceleration data, wherein the body offset angle characterizes a torso offset of the moving person and the velocity unit vector characterizes a direction of travel of the moving person; and
         a velocity component that determines a reference velocity vector that characterizes a speed and direction of travel of the moving person based on the velocity unit vector, the step rate.

2. The system of claim 1, wherein the velocity vector is also based on a predetermined stride length.

3. The system of claim 2, wherein the acceleration data comprises:
   a vertical component that characterizes acceleration in a vertical direction;

a first horizontal component that characterizes acceleration in a first horizontal direction; and a second horizontal component that characterizes acceleration in a second horizontal direction offset about 90 degrees from the first horizontal direction.

4. The system of claim 3, further comprising:

a vertical accelerometer that provides the vertical component of the acceleration data;

a first horizontal accelerometer that provides the first horizontal component of the acceleration data; and a second horizontal accelerometer that provides the second horizontal component of the acceleration data.

5. The system of claim 1, wherein the controller further comprises a Kalman Filter component configured to determine a stride length error of the moving person based on a recursive comparison of the reference velocity vector and a navigation velocity that characterizes an integration of at least a portion of the acceleration data over a predetermined amount of time.

6. The system of claim 5, wherein the controller further comprises a dead reckoning component that determines an offset corrected position of the moving person based on the stride length error, the reference velocity vector and a last known or calculated position of the moving person, wherein the offset corrected position of the moving person characterizes an estimated or calculated position of the moving person.

7. The system of claim 6, further comprising a global positioning system (GPS) configured to receive satellite signals and to determine a position of the moving person based on the received satellite signals.

8. The system of claim 7, wherein the controller is configured to determine the offset corrected position of the moving person if the GPS fails to receive the satellite signals.

9. The system of claim 1, wherein the body offset angle is further based on heading data that characterizes a detected heading of the moving person.

10. A system for tracking a moving person, the system comprising:

a controller configured to receive acceleration data that characterizes an acceleration of the moving person in three dimensions, wherein the controller comprises:

a step rate component that determines a step rate for the person based on a vertical component of the acceleration data;

a body offset component that determines a body offset angle based on a spectral analysis of the acceleration data and the step rate; and a velocity component that determines a reference velocity vector based on the body offset angle and the step rate;

wherein the spectral analysis of the acceleration data includes comparing a signal strength in first and second horizontal components provided from corresponding first and second horizontal accelerometers for signals at a frequency substantially equal to the step rate.

11. The system of claim 10, wherein the signal strength of the first horizontal component varies in inverse proportion to the body offset angle, and the signal strength of the second horizontal component varies in proportion to the body offset angle.

12. An integrated unit that includes the system of claim 11, wherein the integrated unit is detachably affixed to a position at or above a waistline of the moving person.

13. A system for tracking a moving person, the system comprising:

means for providing three dimensional acceleration data that characterizes acceleration of the moving person in three dimensional space;

means for determining a step rate of the moving person based on a vertical component of the three dimensional spectral data; and means for spectrally analyzing the step rate and horizontal components of the three dimensional acceleration data to determine a magnitude of a body offset angle that characterizes a magnitude of a torso offset of the moving person.

14. The system of claim 13, further comprising:

means for determining a body offset angle based on the magnitude of the body offset angle and heading data that characterizes a detected heading of the moving person, wherein the body offset angle characterizes a torso offset of the moving person; and means for determining a velocity unit vector that characterizes the direction of travel of the moving person.

15. The system of claim 14, further comprising means for determining a reference velocity based on the determined body offset angle and the step rate.

16. The system of claim 15, further comprising means for determining a navigation velocity vector based on an integration of at least a portion of the acceleration data over a predetermined amount of time.

17. The system of claim 16, further comprising means for determining a stride length error based on a Kalman Filter recursive comparison of the reference velocity vector and the navigation velocity.

18. A method for tracking a moving person, the method comprising:

determining, at a controller, a step rate for the moving person; and determining, by the controller, a body offset angle for the moving person based on the step rate and a detected heading of the moving person and a spectral analysis of horizontal components of acceleration data that characterizes an acceleration of the moving person in three dimensional space wherein the body offset angle characterizes a torso offset of the moving person.

19. The method of claim 18, further comprising:

determining, by the controller a velocity unit vector based on the body offset angle, the velocity unit vector characterizing a direction of travel of the moving person; and determining, by the controller, a reference velocity of the moving person based on the step rate, and the velocity unit vector.

20. The method of claim 19, further comprising:

determining, by the controller, a navigation velocity of the moving person based on an integration of at least a portion of the acceleration data;

determining, by the controller, a stride length error based on a Kalman Filter recursive comparison of the navigation velocity and the reference velocity; and determining, by the controller, a position of the moving person based on a last known or calculated position of the moving person, the stride length error and the reference velocity.

* * * * *